United States Patent [19]

Hansen

[11] Patent Number: 4,643,678

[45] Date of Patent: Feb. 17, 1987

[54] DENTAL APPLICATION FLUID FOR THE INSPECTION OF TOOTH CONTACTS AND PROSTHETIC WORKS

[75] Inventor: Jens M. Hansen, Bonn, Fed. Rep. of Germany

[73] Assignee: Prodent Ges. Fuer Zahnmed. Bedarfsartikel mbH, Hamburg, Fed. Rep. of Germany

[21] Appl. No.: 696,509

[22] Filed: Jan. 30, 1985

[30] Foreign Application Priority Data

Jan. 30, 1984 [DE] Fed. Rep. of Germany ....... 3403118

[51] Int. Cl.$^4$ .......................... A61K 6/00; A61K 6/02; A61K 6/12
[52] U.S. Cl. .................................... 433/217.1; 106/35; 106/237; 106/241; 523/109; 524/88; 524/413; 433/215
[58] Field of Search .................. 523/120, 109; 524/88, 524/413

[56] References Cited

U.S. PATENT DOCUMENTS

| | | | |
|---|---|---|---|
| 1,889,622 | 11/1932 | Antonucci . | |
| 2,296,877 | 9/1942 | Slack | 260/32 |
| 3,558,540 | 1/1971 | Molnar | 260/23 |
| 3,694,237 | 9/1972 | Piotrowski | 106/30 |
| 4,001,035 | 1/1977 | Ito et al. | 524/563 |
| 4,021,252 | 5/1977 | Banczak et al. | 524/389 |
| 4,145,216 | 3/1979 | Merrill et al. | 430/291 |
| 4,168,662 | 9/1979 | Fell | 106/30 |
| 4,177,075 | 12/1979 | Mansukhani | 106/20 |
| 4,194,921 | 3/1980 | Wheeler et al. | 524/600 |
| 4,369,232 | 1/1983 | Scopazzi | 524/441 |
| 4,391,928 | 7/1983 | Herman et al. | 525/902 |
| 4,408,009 | 10/1983 | Mallon | 524/858 |
| 4,448,796 | 5/1984 | Wieser et al. | 427/212 |
| 4,483,712 | 11/1984 | Murphy | 428/497 |

FOREIGN PATENT DOCUMENTS 800920 12/1950 Fed. Rep. of Germany .

OTHER PUBLICATIONS

"The Chemistry of Synthetic Dyes" vol. V edited K. Venkataraman Academic Press 1971, N.Y. p. 314 1st paragraph.

Primary Examiner—Herbert J. Lilling
Attorney, Agent, or Firm—Schwartz, Jeffery, Schwaab, Mack, Blumenthal & Evans

[57] ABSTRACT

A dental application fluid for the inspection of tooth contacts and prosthetic works comprising an organic, polymeric adhesive (such as shellac), a massive component (such as titanium oxide), and a colored pigment (such as heliogen blue) all dispersed or dissolved in an alcoholic solvent.

15 Claims, No Drawings

DENTAL APPLICATION FLUID FOR THE INSPECTION OF TOOTH CONTACTS AND PROSTHETIC WORKS

BACKGROUND OF THE INVENTION

The invention relates to a new application fluid for dental purposes. The invention may be used by dentists, dental technicians, and other dental health care professionals to determine and check occlusions (contact points), and to form and control approximate contacts and prosthetic works, including inlays, crowns, bridges and the like. The invention may be particularly used for controlling and producing an exact fit for all fixed prosthetic works.

It is known to use a silicon-based compound, which may be packed in tubes, for checking and producing the precision of fit of fixed prosthetic works. The known compound is mixed with a catalyst on a neutral background, such as a glass plate or graduated block. The known compound is then usually introduced into the crown as a viscous, elastic mass by means of a spatula. Subsequently, the crown is set on the stump and pressed tightly. After a setting time of about seven minutes, the application compound becomes hard. This available silicon-based compound requires a considerable expenditure of time and labor in its application; moreover, the available compound is only difficultly measured out.

Occlusion papers, in the form of larger film sheets, or in the form of bands of differing color have been proposed for the inspection and formation of approximate contacts in the occlusion. The colors of these films should represent their strength (thickness). Thick films are used for the rough formation of occlusion points and thinner films are used for finely shaping the occlusion points and articulation points (i.e., those points in contact during lateral and advancing movements of the jaw). Contact points may be determined and inspected by biting down on the teeth and by means of articulation movements. However, occlusion papers of this kind are unsuited for the production and inspection of prosthetic works.

Furthermore, so-called occlusion waxes, available in the form of small plates, are known and have been proposed for the bite (abduction), that is, the occlusion. These occlusion waxes are suited neither for the determination of articulation movements nor for the production and inspection of prosthetic works.

In addition, so-called occlusion sprays with a powdered consistency are known which may be dispensed from a spray can. The granularity of the powder is between 10 and 20 micrometers. Even though occlusion sprays of this kind offer distinct advantages in use, they also have a series of disadvantages. It is hardly possible with occlusion sprays of this kind to achieve an even distribution, because the application would then be too thick. Additionally, these powders lack sufficient adhesive strength on metal, which leads to the result that, even though the powders adhere to the tooth stump, they show insufficient adhesion to the prosthetic metal parts. For this reason, the pressure points may only be very inaccurately determined because the powder already loses its adhesiveness after the slightest contact, and is therefore only actually usable with extremely early contacts. A further disadvantage is that the powder becomes stringy and forms lumpy deposits after the unavoidable contact with saliva, and is thereafter unusable. The occlusion spray is not particularly well removed with water. The powder gives off much dust when applied, so that fingers, hands, and even the local environment are heavily contaminated.

SUMMARY OF THE INVENTION

It is an object of the invention to provide an application compound which is ready to use and therefore directly applicable, non-viscous, fast-drying, and strongly adhesive to metal as well as tooth material. The application compound should be sensitive to contact, easily measured out, compatible with saliva, and yet easily removable. The handling and application of the compound should afford the most economical expenditure of material possible.

This compound should be suitable for the control and inspection of tooth contacts and prosthetic works for all of the above reasons.

To achieve this object, the invention proposes an application fluid which comprises a directly applicable, non-viscous, quick-drying compound, in which an organic, polymeric adhesive, a massive component, and a colored pigment, are dispersed or dissolved in an alcoholic solvent.

The application fluid according to the invention is a directly applicable fluid, which, in contrast to the above-mentioned silicon-based compounds, requires no prior preparation by means of a catalyst. The product is non-viscous and may be applied and distributed without difficulty by means of forceps and a ball of cotton. The application fluid drys fast; the drying time equals only about 5 to 10 seconds and can even be shortened with the use of a hand blower. The application fluid according to the invention adheres to all materials which are used in the dental profession, including tooth materials. The application fluid thereby allows an unusually exact determination of pressure and contact points. The marking of contacts and early contacts is very distinct. The application fluid according to the invention is easily and economically measured out because of its non-viscous consistency and composition. A significantly greater number of crown coatings is therefore achieved in contrast to the above-mentioned occlusion sprays (improvement equals about 350%). The fluid is neither toxic nor does it irritate the pulp. After use, the application fluid is quickly and well-removed from the teeth, crowns and the like with a solvent fluid. String formation and clumping, because of contact with saliva, do not occur during use.

The numerous advantages of the application fluid according to the invention, when compared with the above-mentioned occlusion spray, are represented in the following table.

TABLE

|  | Occlusion Spray | Application fluid according to the invention |
| --- | --- | --- |
| Aggregate | Powder | fluid |
| Soluble in | water: moderately | alcohol: very |
| Granularity | 10–20 μm | under 10 μm |
| Drying time | None | 5–10 s |
| Dosaging | difficult | easy |
| Adhesion to Metals | insufficient | good |
| Distribution | insufficient | good |
| Properties in contact with saliva | string formation and clumping | no negative properties |
| Contact recognition | insufficient, only for extremely early contacts | good |

TABLE-continued

| | Occlusion Spray | Application fluid according to the invention |
|---|---|---|
| Neatness | not neat, creates much dust | neatly used |
| Number of crown brushings per packaging unit | about 100 | about 350 |

Further objects, features and advantages of the present invention will become apparent from the detailed description of preferred embodiments which follows, when considered together with the several non-limiting examples.

DESCRIPTION OF PREFERRED EMBODIMENTS

The application fluid according to the invention contains an organic, polymeric adhesive in dispersed or dissolved form, respectively. The granularity of the adhesive is preferably smaller than 10 micrometers. The adhesive is preferably a natural resin, particularly a resin from the group of shellac resins, colophonium resins, and modified colophonium resins. Another suitable group of adhesives are represented by the group of alkyd resins, polyvinyl acetaldehydes, polyvinyl alcohols, polyvinyl acetates, polyacrylates and ketone resins.

The proportion of organic, polymeric adhesive totals preferably from about 0.5% to about 10% by weight, particularly from about 1% to about 5% by weight, in each case with respect to the total mass.

The massive component is a powdered constituent with a granularity of preferably under 10 micrometers, more preferably 5 to 7 micrometers. The massive component is preferably selected from the group of inert, pharmaceutically compatible pigments. Titanium dioxide, in the form of titanium white, for example, is very much preferred. Titanium white, according to DIN55192 (November, 1960), is a pigment whose color-determining constituent is titanium dioxide. Aside from titanium dioxide, titanium white additionally contains sulfates and carbonates of barium, calcium, and magnesium, and, additionally, for reasons of painting technology, up to 10% zinc oxide (depending on the intended use). The titanium oxide fraction, however, lies above 20% in each case. Anatase and rutile are also contemplated as titanium oxide materials. The fraction of massive component in the application fluid comprises preferably from 35% to 65% by weight, especially 40% to 60% by weight, with respect to the total quantity in each case.

The application fluid according to the invention contains a colored pigment, similar to the above-mentioned silicon compounds, for the visual recognition of contact points. The colored pigment is chosen from the group of physiologically harmless color pigments; and a green, red, or preferably blue color, is produced by contacts. Pigments from the heliogen series are preferably used, i.e., phthalocyanine-based colored pigments. Heliogen blue is a particularly suited pigment. The concentration of the colored pigment is dependent on the intended use, so that dosaging may be carried out in the usual manner. The colored pigment content preferably lies in the range from 0.01% to 10% by weight, preferably 0.1% to 2% by weight, with respect to the total mass in each case.

In addition to the above mentioned significant components of the application fluid, further common components of dental application compounds may be contained, if necessary, which keep the application fluid antiseptic, pyrogen free, and sterile.

The alcoholic solvent of the application fluid is preferably an alcohol, particularly ethanol of cosmetic quality or pure ethanol. Furthermore, other physiologically harmless fluids may be used with alcohol as long as they do not impair the consistency of the application fluid. Consequently, the composition of the application fluid is as follows:

| Weight Fractions | Preferred | Particularly Preferred |
|---|---|---|
| Adhesive | 0.5–10 | 1–5 |
| Massive Component | 35–65 | 40–60 |
| Colored Pigment | 0.01–10 | 0.1–2 |
| Solvent | 30–70 | 40–60 |

Examples for individual preferred compositions of the application fluid according to the invention, and one example each for their use in the examination of the occlusion, the articulation and in the inspection and production of a precise fit in prosthetic works follow.

EXAMPLE 1

Production of the application fluid 3.63 parts by weight shellac (Gombal OD2) are dissolved in 20 parts by weight ethanol, with stirring. In each case, 0.06 parts by weight Bentone W and Bentone 34 (dispersing agents), 48 parts by weight titanium dioxide (RN 56) and 0.25 parts by weight heliogen blue are added to this solution with stirring. The resulting paste is dispersed for 30 minutes in a high speed dissolver. After achieving the desired granual size ($<10\ \mu m$), the remaining quantity of ethanol (28 parts by weight) is added. A non-viscous application fluid results.

EXAMPLE 2

Directed grinding of the inner surface and approximate surfaces of inlays crowns and the like The application fluid of example 1 is purposefully applied to the approximate and chew surfaces by means of forceps and a cotton pellet. After a drying time of about 5 to 10 seconds, the prosthetic replacement is correspondingly inserted, pressed on and again removed.

Early contacts, as well as the precision of fit are visible at the points in which the dried application fluid has been pushed away or is missing, respectively. Grinding work is necessary in these exactly signified points (early contacts) for the production of an optimal precision of fit (removal of the early contacts). Contamination of hands and instruments is easily removed by means of an alcoholic solvent, ethanol for example.

EXAMPLE 3

Inspection or correction (filing in), respectively of the occlusive relationships The application fluid of example 1 is applied to the chewing surface of natural teeth. After the drying time, the patient is allowed to bite down or effect articulation movements (lateral movements), respectively. The occlusion contacts or articulation contacts, respectively, are visible at those points in which the dried application fluid is pushed away. These points allow the even filing in (production of an equalized occlusion and articulation) of individual tooth crowns as well as the entire denture.

EXAMPLE 4

Directed inspection of the bite height with amalgam fillings

After the filling is replaced, it is painted with the application fluid of example 1. The patient is allowed to bite down after the drying time. Should individual larger contact surfaces thereafter be visible on the filling, then these must be reduced with appropriate carving instruments.

EXAMPLE 5

Directed inspection and formation of the approximate surfaces of crowns, bridges and the like The application fluid of example 1 is applied to the entire approximate surface. The prosthetic replacement is correspondingly set in after drying. After removal of the prosthesis, and by means of the size and contour shape of the surface which is pushed away, the contact surface or contact point, respectively, may be inspected and, if necessary, reformed by filing.

What is claimed is:

1. A directly applicable, nonviscous, fast drying dental application fluid for the inspection of tooth contacts and prosthetic works, comprising:
   (a) an organic, polymeric adhesive,
   (b) a massive component, and
   (c) a colored pigment distinct from component (b), said components (a), (b) and (c) being dissolved or dispersed, respectively, in an alcoholic solvent (d), wherein said dental application fluid contains 0.5 to 10 weight fractions of component (a), 0.01 to 10 weight fractions of component (c), and 30 to 70 weight fractions of component (d); and wherein 30 to 70 weight percent of the total application fluid are solids having a granularity of less than 10 microns.

2. An application fluid as recited in claim 1, wherein said adhesive is selected from the group consisting of natural resins and modified natural resins.

3. An application fluid as recited in claim 1, wherein said adhesive is selected from the group consisting of shellac, colophonium resins, and modified colophonium resins.

4. An application fluid as recited in claim 1, wherein said adhesive is selected from the group consisting of alkyd resins, polyvinyl acetaldehydes, polyvinyl alcohols, polyvinyl acetates, polyacrylates and ketone resins.

5. An application fluid as recited in claim 1, wherein said massive component comprises titanium oxide.

6. An application fluid as recited in claim 1, wherein said colored pigment comprises a blue phthalocyanine pigment.

7. An application fluid as recited in claim 1, wherein said fluid comprises from about 1% to about 5% polymeric adhesive, from about 40% to about 60% massive component, from about 0.1% to about 2% colored pigment, and from about 40% to about 60% solvent, wherein said percentages are calculated by weight with respect to the total weight of the solution.

8. An application fluid as recited in claim 7, wherein said polymeric adhesive comprises shellac, wherein said massive component comprises titanium dioxide, wherein said colored pigment comprises heliogen blue, and wherein said solvent comprises ethanol.

9. An application fluid as recited in claim 3, wherein said adhesive comprises shellac.

10. A process for dental inspection, comprising the steps of:
    (a) applying a fluid as defined in claim 1 to the surface of a tooth, crown, bridge or inlay;
    (b) allowing said fluid to dry on said surface;
    (c) applying pressure to said fluid-coated surface to produce pressure and contact points thereon; and
    (d) inspecting said pressure and contact points.

11. An application fluid as recited in claim 1, wherein said massive component is selected from the group consisting of inert, pharmaceutically compatible pigments.

12. An application fluid as recited in claim 11, wherein said massive component is titanium white.

13. A directly applicable, nonviscous, fast drying dental application fluid for the inspection of tooth contacts and prosthetic works, comprising:
    (a) an organic polymeric adhesive,
    (b) a titanium dioxide component, and
    (c) a colored pigment,
       said components (a), (b), (c) being dissolved or dispersed, respectively, in a physiologically harmless alcoholic solvent comprising ethanol, wherein said dental application fluid contains 0.5 to 10 weight fractions of component (a), 0.01 to 10 weight fractions of component (c), and 30 to 70 weight fractions of said alcoholic solvent; and wherein the solids content of the application fluid is 30 to 70 weight percent.

14. An application fluid as recited in claim 13, wherein said titanium dioxide component is titanium white.

15. A process for dental inspection, comprising the steps of:
    (a) applying a fluid as defined in claim 13 to the surface of a tooth, crown, bridge or inlay;
    (b) allowing said fluid to dry on said surface;
    (c) applying pressure to said fluid-coated surface to produce pressure and contact points thereon; and
    (d) inspecting said pressure and contact points.

* * * * *